(12) United States Patent
Ogawa

(10) Patent No.: US 6,531,601 B2
(45) Date of Patent: Mar. 11, 2003

(54) MOLDED CATALYST FOR PRODUCTION OF TRIETHYLENEDIAMINE, METHOD FOR ITS PRODUCTION, AND METHOD FOR PRODUCING TRIETHYLENEDIAMINE

(75) Inventor: Tsukasa Ogawa, Yokohama (JP)

(73) Assignee: Tosoh Corporation, Yamaguchi (JP)

( * ) Notice: Subject to any disclaimer, the term of this patent is extended or adjusted under 35 U.S.C. 154(b) by 0 days.

(21) Appl. No.: 09/961,413

(22) Filed: Sep. 25, 2001

(65) Prior Publication Data

US 2002/0072467 A1 Jun. 13, 2002

(30) Foreign Application Priority Data

Sep. 29, 2000 (JP) ........................................ 2000-302875

(51) Int. Cl.$^7$ ............................ B01J 29/40; B01J 29/06; C07D 487/08
(52) U.S. Cl. ............................ 544/352; 502/64; 502/71
(58) Field of Search ............................ 544/352; 502/64, 502/71

(56) References Cited

U.S. PATENT DOCUMENTS

| 4,548,913 A | * | 10/1985 | Schwerdtel et al. | .......... | 502/71 |
| 4,925,820 A | * | 5/1990 | Hoek et al. | .................... | 502/64 |
| 5,583,081 A | * | 12/1996 | Price et al. | .................... | 502/71 |
| 6,077,984 A | | 6/2000 | Drake et al. | | |
| 6,084,096 A | * | 7/2000 | Li et al. | ..................... | 544/358 |

FOREIGN PATENT DOCUMENTS

| EP | 0 831 096 A2 | 3/1998 |
| EP | 0 952 152 A2 | 10/1999 |
| WO | 00/29511 | 5/2000 |

OTHER PUBLICATIONS

Kirk–Othmen Encyclopedia of Chemical Technology 2nd Edition, 1964, pp. 534–541.

* cited by examiner

Primary Examiner—Mark L. Berch
(74) Attorney, Agent, or Firm—Sughrue Mion, PLLC

(57) ABSTRACT

A molded catalyst for production of triethylenediamine, wherein (1) the main components are silica and crystalline aluminosilicate, (2) the silica is amorphous, and the content of the silica is from 5 to 70 wt %, (3) the molar ratio of silica to alumina in the crystalline aluminosilicate is at least 12, and the content of the crystalline aluminosilicate is from 30 to 95 wt %, and (4) the hardness is at least 1 kg.

17 Claims, No Drawings

MOLDED CATALYST FOR PRODUCTION OF TRIETHYLENEDIAMINE, METHOD FOR ITS PRODUCTION, AND METHOD FOR PRODUCING TRIETHYLENEDIAMINE

The present invention relates to a molded catalyst for production of triethylenediamine, a method for its production, and a method for producing triethylenediamine employing such a catalyst. More particularly, the present invention relates to an improved crystalline aluminosilicate molded catalyst which is capable of producing triethylenediamine effectively and efficiently from an amine compound.

Triethylenediamine is a useful compound which is used in a large amount as e.g. a foaming catalyst in production of polyurethanes or a curing accelerator for epoxy resins.

Such triethylenediamine can be obtained usually by cyclization of an amine compound by using a catalyst. As such a catalyst, zeolite is well known. For example, ① JP-A-62-228079 and ② JP-A-63-122654 disclose a method of using a crystalline metal silicate subjected to calcination treatment in an air atmosphere at a temperature of from 400 to 600° C. and having a molar ratio of silica to alumina of at least 12, as a catalyst; ③ JP-A-1-132587 discloses a method of using a pentasyl-type zeolite as a catalyst; ④ JP-A-1-143864 discloses a method of using a pentasyl-type zeolite as a catalyst and contacting ethylenediamine, diethylenetriamine or 2-aminoethanol with such a catalyst at a temperature of from 250 to 550° C. to obtain triethylenediamiine; ⑤ JP-A-3-133971 discloses a method of employing a pentasyl-type zeolite containing an alkali metal or having aluminum in the zeolite framework isomorphically substituted by iron, as a catalyst, and contacting ethylenediamine with the catalyst at a temperature of from 270 to 420° C. to obtain triethylenediamine; ⑥ JP-A-5-17460 discloses a method for producing triethylenediamine from an amine compound and a catalyst composed of a crystalline aluminosilicate subjected to calcination treatment at a temperature of from 500 to 950° C. in a steam atmosphere; ⑦ JP-A-5-17461 discloses a method for producing triethylenediamine from an amine compound and a catalyst composed of a crystalline aluminosilicate subjected to calcination treatment at a temperature of from 610 to 950° C. in an air atmosphere; ⑧ JP-A-5-17462 discloses a method for producing triethylenediamine from an amine compound and a crystalline aluminosilicate catalyst having an inorganic salt supported thereon; ⑨ JP-A-10-109964 discloses a method for producing triethylenediamine from an amine compound and a zeolite catalyst subjected to basic treatment; ⑩ JP-A-10-182562 discloses a method for producing triethylenediamine from an amine compound and a surface acidity-deactivated zeolite catalyst; and ⑪ JP-A-10-195029 discloses a method for producing triethylenediamine from a triethylenediamine reaction solution having an ethylated compound and a zeolite having a shape selectivity for a condensation reaction and a cyclic reaction added.

As mentioned above, many methods employing zeolite catalysts have been disclosed for the production of triethylenediamine. However, such zeolite catalysts had the following problems when used as industrial catalysts.

In the methods for producing triethylenediamine, the reaction system may be either a batch system, a semibatch system or a continuous system, and the reaction can be carried out in a suspension bed system (a fluidized bed system in the case of a gas phase reaction) or a fixed bed flow system. However, industrially, the fixed bed flow system is advantageous from the viewpoints of operation, apparatus and economical efficiency. In all of Working Examples of the above-mentioned prior art, the reaction is carried out by a fixed bed flow system. In the case of a fixed bed flow system, not only the yield of triethylenediamine, but also the mechanical strength of the molded catalyst and the catalyst life, are very important. With respect to the preparation of the molded catalyst, the prior art gives little specific description of e.g. the molding method, the binder, etc., and has not yet reached a level which is applicable to an industrial fixed bed flow system continuous reactor.

Only ⑥ JP-A-5-17460, ⑦ JP-A-5-17461 and ⑧ JP-A-5-17462 disclose molding methods. These publications mention about extrusion molding, tableting and granulation, but in all Working Examples, tableting is employed.

With respect to the description of a binder, ② JP-A-63-122654 discloses silica, alumina, silica-alumina, etc., ⑤ JP-A-3-133971 discloses alumina oxide, silicon dioxide or a clay such as bentonite or montmorillonite, ⑥ JP-A-5-17460, ⑦ JP-A-5-17461 and ⑧ JP-A-5-17462 disclose silica, alumina, silica-alumina, clay, etc., and ⑨ JP-A-10-109964, ⑩ JP-A-10-182562 and ⑪ JP-A-10-195029 disclose silica, alumina, titania, zirconia and natural clay, but no specific disclosure is made in Working Examples. ③ JP-A-1-132587 and ④ JP-A-1-143864 mention about an inert binder in Working Examples, but no name of the material is disclosed. Further, ⑨ JP-A-10-109964, ⑩ JP-A-10-182562 and ⑪ JP-A-10-195029 disclose that a material having a low acidity such as silica or zirconia is preferred, since an undesirable side reaction caused by a more active material such as alumina, can be prevented. However, no specific operation or effects are described.

Further, with respect to the yield of triethylenediamine and the catalyst life when triethylenediamine is prepared by means of such a catalyst, for example, by the method disclosed in ① JP-A-62-228079 or ② JP-A-63-122654, the selectivity of triethylenediamine can be increased if the conversion of the starting material is made low, but the selectivity decreases as the conversion increases, and thus, it is not possible to obtain triethylenediamine in good yield, and the decrease in activity of the catalyst with time is significant. By the method disclosed in ③ JP-A-1-132587 or ④ JP-A-1-143864, the selectivity for triethylenediamine is high, but the conversion of the starting material at that time is low, whereby the yield of triethylenediamine is low, and deterioration with time of the catalytic activity is substantial. By the method of employing an alkali metal ion-containing pentasyl type zeolite as disclosed in ⑤ JP-A-3-133971, the selectivity is high, but the conversion of the starting material is low, and the yield of triethylenediamine is low. On the other hand, with the pentasyl-type zeolite having aluminum in the zeolite framework substituted by iron, the selectivity is high, and as a result, the yield is improved, but the catalyst is a special zeolite, and the method for its production is complex, and the production conditions are severe, the production costs are high, such being not practical from the industrial viewpoint. Although the deterioration with time of the catalytic activity is lower than other conventional catalysts, the improvement is not yet of a level satisfactory from the industrial point of view.

By the method disclosed in ⑥ JP-A-5-17460, ⑦ JP-A-5-17461 or ⑧ JP-A-5-17462, the yield of triethylenediamine is improved, but deterioration with time of the catalytic activity is substantial.

By the method disclosed in ⑨ JP-A-10-109964 or ⑩ JP-A-10-182562, the yield of triethylenediamine is low, and deterioration with time of the catalytic activity is substantial, and such a method is not useful as an industrial production method.

Further, the method disclosed in JP-A-10-195029 is a two step reaction, whereby the operation is cumbersome, the installation cost tends to be high, and deterioration of the catalytic activity is also substantial. In the foregoing, various problems of the methods for producing triethylenediamine employing conventional catalysts, have been described, but these problems may be summarized into the following three categories.

(1) The molded catalyst has low strength and is likely to disintegrate into fine powder during the reaction, whereby continuation of the operation becomes impossible. This brings about an increase of the operation pressure especially when the reaction is carried out in a fixed bed flow system, which will be a fatal drawback.

(2) The yield of triethylenediamine in the catalytic reaction is low, such being uneconomical. This brings about not only deterioration of the productivity but also cumbersomeness in the separation and purification of triethylenediamine, and deterioration in the purity of the triethylenediamine product.

(3) Deterioration with time of the catalytic activity is substantial, whereby an industrial stabilized operation tends to be difficult, and the production efficiency tends to be low. This means that the catalyst life is short, thus leading to an increase of the cost for the catalyst and an increase of the work load of replacing the catalyst. Thus, this is a serious problem which must be solved, for the catalytic reaction.

Namely, development of a technique to solve these three problems has been strongly desired for the production of industrially useful triethylenediamine.

The present inventors have conducted an extensive study for a long period of time on the search for a catalyst, on the preparation of the catalyst and on the production of triethylenediamine using the catalyst, in an attempt to find out a technique which is capable of solving the above three problems simultaneously. As a result, they have found a clue for solving the problems by a molded catalyst having a certain specific composition and a specified strength and have finally accomplished the present invention.

Namely, the present invention provides a molded catalyst for production of triethylenediamine, characterized in that (1) the main components are silica and crystalline aluminosilicate, (2) the silica is amorphous, and the content of the silica is from 5 to 70 wt %, (3) the molar ratio of silica to alumina in the crystalline aluminosilicate is at least 12, and the content of the crystalline aluminosilicate is from 30 to 95 wt %, and (4) the hardness is at least 1 kg.

The present invention also provides a method for producing such a molded catalyst for production of triethylenediamine, characterized in that amorphous silica composed of primary particles having an average particle size of from 6 to 60 nm, is used as a binder, and the silica and crystalline aluminosilicate are mixed and then molded into a uniformed shape by a molding machine.

Further, the present invention provides a method for producing triethylenediamine, characterized by contacting at least one member selected from the group consisting of amine compounds having a group represented by the following formula (1):

—CHR$^1$—CHR$^2$—NR$^3$R$^4$     (1)

wherein each of R$^1$ to R$^4$ which are independent of one another, is a hydrogen atom or a C$_{1-3}$ alkyl group which may have a substituent, with such a molded catalyst for production of triethylenediamine.

Now, the present invention will be described in further detail.

Firstly, the molded catalyst for production of triethylenediamine of the present invention will be described.

The catalyst of the present invention comprises silica and crystalline aluminosilicate as the main components. It may further contain a small amount of inorganic compounds and/or organic compounds.

In the present invention, the silica to be used for the catalyst is amorphous and is not crystalline like quartz or cristobalite. This can be easily determined by a powder X-ray diffraction apparatus. When the silica is amorphous, a molded catalyst having a high hardness and a long catalytic life, which are characteristics of the present invention, can be obtained.

In the present invention, the content of silica in the catalyst is from 5 to 70 wt %. If it is less than 5 wt %, a molded catalyst having an industrial hardness may not be obtained, and if it exceeds 70 wt %, the catalytic activity of the molded catalyst tends to decrease. A preferred content is from 15 to 50 wt %. In a case where the main component is not silica but clay or alumina, the hardness of the molded product may be high, but the catalyst life is very short, and such is not included in the present invention.

In the present invention, the active species of the catalyst is crystalline aluminosilicate, and the molar ratio of silica to alumina in this crystalline aluminosilicate is at least 12. If the molar ratio is less than 12, the selectivity for triethylenediamine tends to deteriorate, and an unnecessary byproduct tends to form in a large amount. A preferred molar ratio is from 40 to 5,000, whereby the catalytic activity is high, the selectivity for triethylenediamine is high, and the catalyst life can be prolonged, such being economical. If the molar ratio exceeds 5,000, the catalyst activity tends to decrease, or preparation of such crystalline aluminosilicate tends to be difficult.

In the present invention, the content of the crystalline aluminosilicate in the catalyst is from 30 to 95 wt %. If it is less than 30 wt %, the catalytic activity tends to deteriorate, and if it exceeds 95 wt %, the hardness of the molded catalyst tends to deteriorate. A preferred content is from 50 to 85 wt %, whereby an industrially preferred molded catalyst for triethylenediamine will be obtained.

In the present invention, the crystalline aluminosilicate is preferably one having a main cavity of oxygen ten-membered ring, whereby the catalytic activity and the catalyst life can be increased. Its specific examples include ZSM-5 as disclosed in U.S. Pat. No. 3,702,886, ZSM-8 as disclosed in U.S. Pat. No. 1,334,243, ZSM-11 as disclosed in U.S. Pat. No. 3,709,979, ZSM-12 as disclosed in U.S. Pat. No. 3,832,449, and ZSM-21 as disclosed in U.S. Pat. No. 4,001,346. Among them, ZSM-5 is preferred from the viewpoint of the catalytic activity and the industrial production. Such crystalline aluminosilicate can be obtained usually by hydrothermal synthesis, in which an organic crystallizing agent may or may not be used, and one obtained by any method may be used in the present invention. Further, cations of the crystalline aluminosilicate may not be limited to H-type, and some or all of hydrogen ions may be exchanged with other cations, such as lithium ions, sodium ions, potassium ions, cesium ions, magnesium ions, calcium ions or lanthanum ions. Particularly preferred is crystalline aluminosilicate having ion exchanged with alkali metal ions, particularly sodium ions or potassium ions, from the viewpoint of high yield and suppression of deterioration of the catalytic activity with time.

In the present invention, it is important that the hardness of the catalyst is at least 1 kg. When the hardness is at least 1 kg, it is possible to produce triethylenediamine industrially constantly without disintegration or breakage of the molded catalyst. This is a feature of the catalyst of the present invention and brings about a significant effect when a fixed bed flow system reactor is employed. In the present invention, the hardness means a hardness measured by a crushing strength test method in accordance with "Granules and agglomerates-Test methods for strength" of JIS Z8841 (1993) which is widely used for the measurement of the strength of a molded product. As a testing device for this crushing strength test method, any device corresponding to the testing device as prescribed in "3.1.1. Testing device" of JIS Z8841 may be employed without any particular restriction. As such a testing device, a Kiya model hardness meter is, for example, preferred. A manual type and an automatic type are available for the Kiya model hardness meter, and either one can be used with good precision. The press chip here is a standard of 5 mm in diameter, which is suitable for measuring molded products of various shapes. The hardness in the present invention represents a value measured by this Kiya model hardness meter with a press chip of 5 mm in diameter. This hardness is preferably from 2 to 20 kg, whereby the molded catalyst can be used constantly for a long period of time even under severe conditions. If the hardness is too high, not only a special apparatus will be required for molding, but also the activity of the molded catalyst tends to be low to some extent, probably because the pore volume of the molded catalyst decreases. More preferably, the hardness is from 3 to 15 kg.

In the present invention, the shape of the molded catalyst is not particularly limited. However, from the viewpoint of production efficiency, handling efficiency, stability of the shape of the molded product during the preparation of triethylenediamine and maintenance of the catalytic activity, it is preferably spherical, oval or cylindrical, and its average diameter as a sphere is preferably from 1 to 20 mm. If the shape is irregular and has many angular corners, breakage is likely to take place during handling or during operation, thus leading to an increase of the operation pressure due to the formed powder. The average diameter as a sphere is an average diameter obtained by calculating the volume from the geometrical shape of the molded product as a sphere. Here, some examples of the relation between the size of a cylindrical molded product and the average diameter as a sphere, are shown in Table 1.

TABLE 1

| Size of a molded product | Average diameter as a sphere |
| --- | --- |
| 1 mm φ × 5 mmL | 2.0 mm φ |
| 1 mm φ × 10 mmL | 2.5 mm φ |
| 3 mm φ × 5 mmL | 5.1 mm φ |
| 5 mm φ × 20 mmL | 9.1 mm φ |
| 10 mm φ × 20 mmL | 14.4 mm φ |

In the present invention, this average diameter as a sphere is more preferably from 2 to 10 mm, whereby the above-mentioned effects can be obtained at a higher level. If the average diameter as a sphere is small, the hardness decreases, or the pressure loss of the catalyst layer increases. On the other hand, if the average diameter as a sphere is large, the hardness will be high, but the apparent specific area decreases, whereby the catalytic performance decreases. Further, drift of the product and starting material for the production of triethylenediamine will take place, whereby the reaction efficiency decreases.

Now, a method for producing the molded catalyst for production of triethylenediamine of the present invention will be described.

For the production of the catalyst of the present invention, firstly amorphous silica composed of primary particles having an average particle size of from 6 to 60 nm, is used as a binder, and such silica and crystalline aluminosilicate are mixed. It is possible to obtain a molded catalyst having a good shape and high hardness, when such amorphous silica composed of primary particles of from 6 to 60 nm, is used as the binder. If the primary particle size of such silica is smaller than 6 nm, the mixing and molding operation tends to be difficult, and it will be difficult to increase the hardness of the molded product. Further, the catalytic activity of the molded product tends to be low, and the catalyst life tends to be short. The reason may be such that since the primary particle size of the silica is small, the pore size of the molded catalyst will be small, whereby the reactivity decreases. On the other hand, if the primary particle size is larger than 60 nm, the mixing and molding operation may be easy, but the hardness of the molded product tends to be small, and disintegration or breakage tends to occur during use of the molded product. Such a primary particle size can easily be measured and identified by SEM (scanning electron microscope) or TEM (transmission electron microscope). Further, the average size of the primary particles can also be obtained from the measurement of the specific surface area by e.g. a BET apparatus, because the primary particles of silica such as colloidal silica, wet process silica and dry process silica are spherical in most cases, and even if their average particle size is obtained from the specific surface area and the true density as spheres, an error is small. This relation may be represented by the following formula:

$$D = \frac{6}{2.2 S} \times 10^3$$

where

D: Average primary particle size (nm) of silica

S: Specific surface area (m$^2$/g) of silica 2.2: True density (g/cm$^3$) of silica, which may vary depending on hydrous or anhydrous, but here 2.2 g/cm$^3$ was employed.

6: Shape factor (–) of spheres

From this formula, the specific surface area of silica having an average primary particle size of from 6 to 60 nm is calculated to be from 50 to 500 m$^2$/g. This is effective for selection of silica to be used.

In the method of the present invention, this silica binder is amorphous and consists essentially of silica, and its silica content is preferably at least 90%. It may contain, as trace constituents, oxides of alkali metals, alkaline earth metals or transition metals. More preferably, the silica content is at least 95 wt %.

In the method of the present invention, as such a silica binder, at least one member selected from the group consisting of colloidal silica, wet process silica and dry process silica, is preferred. Each of them is amorphous. Colloidal silica can be produced by e.g. an ion exchange method, and it is one having spherical primary particles mono-dispersed in an aqueous solution. As commercial products, LUDOX, SYTON, NALCOAG, SNOWTEX, etc., are available. The silica concentration in such colloidal silica is usually from 10 to 50 wt %. Wet process silica is produced by treating an aqueous sodium silica solution with a mineral acid such as sulfuric acid to precipitate silica, and it is called also as white carbon. This is a hydrous silicic acid, and as commercial products, Hi-Sil, Ultrasil, Vulcasil, Santocel, ValronEstersil, Tokusil, Nipsil, etc., are available. Dry process silica is produced by hydrolyzing mainly silicon tetrachloride gas at a high temperature in an oxygen atmosphere, and it is called also as fumed silica. This is anhydrous silicic acid, and as commercial products, Aerosil, Reolosil, Cab-O-Sil, Fransil, DC. Silica, ArcSilica, etc., are available. Among these silicas, colloidal silica is preferred, whereby mixing and molding operation are easy, and a molded product having higher hardness can be obtained. Further, its catalytic performance is high, and the catalyst life can be particularly prolonged.

In the method of the present invention, mixing of the silica and crystalline aluminosilica is not particularly limited so long as they can be uniformly mixed. The apparatus may, for example, be a rotating container type mixer of e.g. cylindrical form, V form, cubic form, double circular cone form, hexagonal form or pyramid form, a fixed container type mixer such as a screw mixer, a ribbon mixer, a Henschel mixer or a rotation pan mixer, or a mixing/kneading machine such as a plast mill. In this mixing operation, it is preferred to use water, whereby mixing can be made more uniformly, and the mixture will have tenacity, whereby the subsequent molding will be facilitated. Further, at the time of mixing, an organic binder such as gum arabic, sodium alginate, processed starch, sodium casein, sodium carboxymethyl cellulose, glycerol, gelatin, starch, molasses, fine crystalline cellulose, pitch, hydroxypropyl cellulose, phenol resin, sodium polyacrylate, polyethylene glycol, polyvinyl alcohol, polyvinyl pyrrolidone, methyl cellulose or lignin, may be added, so that the subsequent molding operation will be improved.

In the method of the present invention, the mixture thus obtained, will then be molded. For the molding, a dry method and a wet method are available, and either method may be used for the present invention. Specifically, the molding method may, for example, be extrusion molding, tableting, tumbling granulation, agitation granulation or roll pressing, and any one of them may be used in the present invention. The shape of the molded product to be obtained by such molding will be spherical, oval, cylindrical or tablet-form, and any one of them may be used in the present invention. With respect to the size, the average diameter as a sphere is preferably from 1 to 20 mm, more preferably from 2 to 10 mm. In the case of dry molding, it is preferred to calcine the molded product, whereby the hardness of the molded product will be improved. In the case of wet molding, it is preferred to dry the molded product, followed by calcination, whereby the hardness of the molded product will be further improved.

In the method of the present invention, a preferred embodiment of mixing and molding is such that wet mixing employing water, is followed by extrusion molding and then by drying and calcination, whereby it is possible to obtain a molded catalyst for production of triethylenediamine, having high hardness and good catalytic performance. A molded product obtained by wet molding is usually dried. The drying temperature is usually from 40 to 200° C., and the drying time is usually from 1 to 24 hours. The atmosphere at that time may be nitrogen, air or the like. In a preferred embodiment, calcination is carried out after molding or drying.

In the method of the present invention, calcination may be carried out in an air atmosphere or in a steam atmosphere. The calcination conditions vary depending upon the type of crystalline aluminosilica, the molar ratio of silica to alumina thereof, the type of an organic crystallizing agent employed, the type of the binder for molding, etc. However, in any case, the temperature is preferably from 500 to 950° C. A more preferred temperature is from 550 to 850° C. The calcination time is usually at least 1 hour, preferably at least 3 hours. If the calcination temperature is low, for example, at a level of lower than 500° C., the hardness of the molded catalyst tends to be slightly low. Further, the selectivity for triethylenediamine as the desired product, tends to be slightly low. On the other hand, if the calcination temperature is high, for example, at a level of higher than 950° C., the crystallizability of the crystalline aluminosilicate deteriorates due to the heat, and the specific surface area tends to be small, whereby the activity as a catalyst deteriorates. At a temperature of from 550 to 850° C., it is possible to obtain a molded catalyst for production of triethylenediamine, which is excellent in the catalytic activity, the catalyst life and the hardness.

In the method of the present invention, after calcination of the molded product, post treatment such as ion exchange may be carried out. The ion exchange operation may be carried out at any stage during the production of the molded catalyst. However, it is preferably carried out after calcination, whereby the operation is easy, and the performance of the molded catalyst can further be increased. Cations of crystalline aluminosilicate after the ion exchange may be at least one type selected from the group consisting of hydrogen ions, lithium ions, sodium ions, potassium ions, cesium ions, magnesium ions, calcium ions and lanthanum ions. Among them, alkali metal ions, particularly sodium ions or potassium ions, are preferred, whereby a high yield and high catalytic activity with time, can be obtained for the production of triethylenediamine.

Now, a method for producing triethylenediamine employing the molded catalyst of the present invention, will be described.

The compound used as a starting material in the method of the present invention is an amine compound having a group represented by the following formula (1):

$$—CHR^1—CHR^2—NR^3R^4 \qquad (1)$$

wherein each of $R^1$ to $R^4$ which are independent of one another, is a hydrogen atom or a $C_{1-3}$ alkyl group which may have a substituent. The compound may, for example, be monoethanolamine, diethanolamine, isopropanolamine, diisopropanolamine, N-(2-aminoethyl)ethanolamine, N-(2-hydroxyethyl)piperazine, N,N'-bis(2-hydroxyethyl)piperazine, N-(2-aminoethyl)piperazine, N,N'-bis(2-aminoethyl)piperazine, piperazine, ethylenediamine, diethylenetriamine, triethylenetetramine or tetraethylenepentamine, and any of these may be used. Among these, a chain ethyleneamine such as ethylenediamine, diethylenetriamine, triethylenetetramine or tetraethylenepentamine, or a cyclic ethyleneamine such as N-(2-aminoethyl)piperazine or piperazine is preferred, since not only it is available in a large amount at a low cost, but also triethylenediamine and piperazine can be produced in higher yields. The more preferred ethyleneamine is N-(2-aminoethyl)piperazine. Such amine compounds may be used alone or in combination as a mixture of two or more of them.

In the method of the present invention, the reaction is carried out in a fixed bed flow system, and it may be carried out either in a gas phase or in a liquid phase.

It is advantageous to carry out the reaction by a gas phase system from the viewpoint of operation, yield and stability of the catalyst. In such a case, as the diluent for the amine compound, a gas such as nitrogen gas, hydrogen gas, ammonia gas, water vapor or a hydrocarbon, may be employed. Otherwise, a solvent such as water or a hydrocarbon, may be employed to dilute the amine compound, and the diluted amine compound may be introduced as the starting material and gasified in the reactor. Such a diluent may be used in an optional amount, and usually the molar ratio of the amine compound to the diluent is preferably from 0.01 to 1. If the molar ratio is smaller than 0.01, productivity of triethylenediamine tends to be low. On the other hand, if the molar ratio is larger than 1, the selectivity for triethylenediamine will slightly decrease.

In the present invention, an amine compound is used as the starting material and contacted with the above molded catalyst to produce triethylenediamines. The reaction conditions such as the reaction temperature and the space velocity at that time, vary depending upon e.g. the types of the crystalline aluminosilicate and the amine compound, and can not absolutely be determined. Usually the reaction is suitably carried out at a reaction temperature of from 250 to 450° C. at a space velocity (GHSV) of from 100 to 10,000 hr$^{-1}$. Further, the reaction may be carried out under either atmospheric pressure, elevated pressure or reduced pressure.

By this catalyst reaction, triethylenediamine can be obtained effectively and efficiently. At that time, piperazine is also obtained as a byproduct. Piperazine is also a useful compound like triethylenediamine, and is useful also as a starting material for production of triethylenediamine.

Further, the molded catalyst of the present invention has high hardness and a long catalyst life, as compared with conventional catalysts. Accordingly, it undergoes gradual deterioration of the catalytic activity by the reaction for a very long period of time. However, by removing organic components attached to the catalyst by calcination, it can be reproduced as a highly active catalyst and can be repeatedly used. This indicates that the catalyst is not essentially changed, and this is an important feature of the present invention. For the activation of the used catalyst, a calcination temperature of at least 500° C. is usually preferred.

Now, the present invention will be described in further detail with reference to Examples. However, it should be understood that the present invention is by no means restricted to such specific Examples.

EXAMPLE 1

100 Parts by weight of powder ZSM-5 type zeolite (860 NHA, manufactured by TOSOH CORPORATION, molar ratio of silica/alumina: 72), 33 parts by weight, as calculated as silica, of colloidal silica having a primary particle size of from 10 to 20 nm (manufactured by Nissan Chemical Industries, Ltd.) as a binder, an organic binder and water, were uniformly mixed and kneaded. Then, by an extrusion machine, a cylindrical molded product of 1.5 mm in diameter×3 to 10 mm in length, was obtained. The molded product was then dried at 120° C. for 4 hours, followed by calcination in a steam atmosphere at 750° C. for 4 hours to obtain ZSM-5(1). This product was measured by a Kiya model hardness meter, whereby the hardness was 2.5 kg on average, and it was confirmed to be a sound molded product.

Into a fixed bed flow system reaction tube, this ZSM-5(1) was packed, and while maintaining the reaction temperature at 355° C., a mixture (N-AEP/water (molar ratio)=8/92) comprising N-(2-aminoethyl)piperazine (N-AEP) and water, was supplied at GHSV1000 hr$^{-1}$. The reaction solution was analyzed by gas chromatography. At the initial stage of the reaction, the conversion of N-AEP was 100%, and the yield of triethylenediamine (hereinafter referred to simply as TEDA) was 54.5 wt %, and the yield of piperazine (hereinafter referred to simply as P) was 18.0 wt %. Thus, both yields were high.

Further, on the seventh day after initiation of the reaction, the reaction temperature was 355° C., the conversion of N-AEP was 100%, and the yield of TEDA was 54.0%, and the yield of P was 18.3 wt %. Thus, both yields were constant at high levels. On the 34th day after the initiation of the reaction, the reaction temperature was higher at 380° C., the conversion of N-AEP was 98.6%, and the yield of TEDA was 45.6 wt %, and the yield of P was 22.7 wt %. Thus, the high catalytic activity was maintained for a long period of time. During this period, no disintegration or breakage of the molded catalyst was observed, and no change was observed in the pressure difference during the reaction.

Further, the catalyst was calcined in an air atmosphere at 600° C. for 4 hours and used again for the reaction. As a result, the reaction results of the fresh catalyst were reproduced. Further, no breakage of the catalyst was observed.

COMPARATIVE EXAMPLE 1

ZSM-5(2) was obtained in the same manner as in Catalyst Preparation Example 1 except that colloidal silica having a primary particle size of from 4 to 6 nm (manufactured by Nissan Chemical Industries, Ltd.) was used as an inorganic binder. The hardness of the molded product by a Kiya type hardness meter was low at a level of 0.7 kg on average.

Production of TEDA was carried out in the same manner as in Example 1 except that ZSM-5(1) was changed to this ZSM-5 (2). At the initial stage of the reaction, the reaction temperature was 355° C., the conversion of N-AEP was 91.3%, and the yield of TEDA was 45.7 wt %, and the yield of P was 15.1 wt %. Thus, the yields were low. Further, on the 15th day after the initiation of the reaction, the reaction temperature was increased to 380°C., and even then, the conversion of N-AEP was 88.9%, and the yield of TEDA was 41.1 wt %, and the yield of P was 17.0 wt %. Thus, the performance deteriorated quickly. Further, the pressure difference of the reaction tube also increased, and the reaction was terminated here. The nitrogen gas was circulated to the reactor for cooling, and the catalyst was taken out, whereby it was mostly in a disintegrated state.

COMPARATIVE EXAMPLE 2

ZSM-5(3) was obtained in the same manner as in Catalyst Preparation Example 1 except that colloidal silica having a primary particle size of from 70 to 100 nm (manufactured by Nissan Chemical Industries, Ltd.) was used as an inorganic binder. The hardness of the molded product by a Kiya model hardness meter was low at a level of 0.6 kg on average.

Production of TEDA was carried out in the same manner as in Example 1 except that ZSM-5(1) was changed to this ZSM-5(3). At the initial stage of the reaction, the reaction temperature was 355° C., the conversion of N-AEP was 97.1%, and the yield of TEDA was 49.3 wt %, and the yield of P was 15.7 wt %. Thus, the yields were low. Further, the pressure difference of the reaction tube increased with time, and consequently, the reaction was terminated on the 5th day. Nitrogen gas was fed to the reaction tube for cooling, and the catalyst was taken out, whereby it was mostly in a disintegrated state.

COMPARATIVE EXAMPLE 3

ZSM-5(4) was obtained in the same manner as in Catalyst Preparation Example 1 except that 33 parts by weight of VOLCLAY was used as an inorganic binder. The hardness of the molded product by a Kiya model hardness meter was 3.8 kg on average.

Production of TEDA was carried out in the same manner as in Example 1 except that ZSM-5(1) was changed to this ZSM-5(4). At the initial stage of the reaction, the reaction temperature was 355° C., the conversion of N-AEP was 100%, and the yield of TEDA was 54.0 wt %, and the yield of P was 18.8 wt %. Thus both yields were high.

However, on the seventh day after the initiation of the reaction, the conversion of N-AEP was 89.0%, and the yield of TEDA was 43.1 wt %, and the yield of P was 17.8 wt %. Thus, the performance deteriorated quickly.

The present invention provides a molded catalyst for production of triethylenediamine, which is important as an industrial catalyst and which has high hardness and high catalytic activity and has little decrease with time of the catalytic activity (a long useful life). Further, it provides a reasonable method for producing the molded catalyst, and further provides a method for effectively and efficiently producing triethylenediamine using the catalyst.

The effects of the present invention will be listed below.
(1) The molded catalyst for triethylenediamine of the present invention is a novel molded catalyst having its constituting components and hardness defined.
(2) The molded catalyst for triethylenediamine having a high performance, can be produced in a large amount inexpensively with good operation efficiency without requiring a special material or operation.
(3) The mechanical strength of the molded catalyst is high, and the molded product is free from disintegration or breakage even if triethylenediamine is produced industrially for a long period of time.
(4) The molded catalyst has high catalytic activity, and deterioration with time of the catalytic activity is very small, whereby triethylenediamine can be produced in good yield and with high productivity for a long period of time.
(5) In the present invention, many amine compounds can be used as starting materials, and thus the present invention has a wide range of applications and thus has a high industrial value.
(6) The molded catalyst of the present invention is substantially free from deterioration in the production of triethylenediamine, can be activated simply by calcination and has high economical efficiency.

The entire disclosure of Japanese Pat. Application No. 2000-302875 filed on Sep. 29, 2000 including specification, claims and summary are incorporated herein by reference in its entirety.

What is claimed is:

1. A molded catalyst for production of triethylenediamine, consisting essentially of (1) as the main components silica and crystalline aluminosilicate, (2) wherein the silica is amorphous, and the content of the silica is from 5 to 70 %, (3) wherein the molar ratio of silica to alumina in the crystalline aluminosilicate is at least 12, and the content of the crystalline aluminosilicate is from 30 to 95 wt %, and (4) wherein the hardness is at least 1 kg.

2. The molded catalyst for production of triethylenediamine according to claim 1, wherein the content of the silica is from 15 to 50 wt %, and the content of the crystalline aluminosilicate is from 50 to 85 wt %.

3. The molded catalyst for production of triethylenediamine according to claim 1, wherein the crystalline aluminosilicate has an oxygen ten-membered ring.

4. The molded catalyst for production of triethylenediamine according to claim 3, wherein the crystalline aluminosilicate having an oxygen ten-membered ring structure is ZSM-5.

5. The molded catalyst for production of triethylenediamine according to claim 1, wherein the molar ratio of silica to alumina in the crystalline aluminosilicate is from 40 to 5,000.

6. The molded catalyst for production of triethylenediamine according to claim 1, wherein the hardness is from 2 to 20 kg.

7. The molded catalyst for production of triethylenediamine according to claim 1, wherein the molded catalyst is spherical, oval or cylindrical, and its average diameter as a sphere is from 1 to 20 mm.

8. The molded catalyst for production of triethylenediamine according to claim 7, wherein the molded catalyst is cylindrical, and its average diameter as a sphere is from 2 to 10 mm.

9. A method for producing a molded catalyst for production of triethylenediamine, wherein amorphous silica composed of primary particles having an average particle size of from 6 to 60 nm, is used as a binder, and the silica and crystalline aluminosilicate are mixed and then molded into a predetermined shape by a molding machine, which molded catalyst consists essentially of (1) as the main components silica and crystalline aluminosilicate, (2) wherein the silica is amorphous, and the content of the silica is from 5 to 70 wt %, (3) wherein the molar ratio of silica to alumina in the crystalline aluminosilicate is at least 12, and the content of the crystalline aluminosilicate is from 30 to 95 wt %, and (4) wherein the hardness is at least 1 kg.

10. The method for producing the molded catalyst for production of triethylenediamine according to claim 9, wherein the mixing of the silica and crystalline aluminosilicate is carried out in a wet system using water, and the molding by a molding machine is followed by drying.

11. The method for producing the molded catalyst for production of triethylenediamine according to claim 9, wherein after the molding, the obtained molded product is calcined at a temperature of from 500 to 950° C.

12. The method for producing the molded catalyst for production of triethylenediamine according to claim 9, wherein the amorphous silica is at least one member selected from the group consisting of colloidal silica, wet process silica and dry process silica.

13. The method for producing the molded catalyst for production of triethylenediamine according to claim 12, wherein the amorphous silica is colloidal silica.

14. The method for producing the molded catalyst for production of triethylenediamine according to claim 9, wherein the molding machine is an extrusion molding machine.

15. A method for producing triethylenediamine, which comprises contacting at least one member selected from the group consisting of monoethanolamine, diethanolamine, isopropanolamine, diisopropanolamine, N-(2-aminoethyl) ethanolamine, N-(2-hydroxyethyl)piperazine, N,N'-bis(2-hydroxyethyl)piperazine, N-(2-aminoethyl)piperazine, N,N'-bis(2-aminoethyl)piperazine, piperazine, ethylenediamine, diethylenetriamine, triethylenetetramine and tetraethylenepentamine, with a molded catalyst for production of triethylenediamine consisting essentially of (1) as the main components silica and crystalline aluminosilicate, (2) wherein the silica is amorphous, and the content of the silica is from 5 to 70 wt %, (3) wherein the molar ratio of silica to alumina in the crystalline aluminosilicate is at least 12, and the content of the crystalline aluminosilicate is from 30 to 95 wt %, and (4) wherein the hardness is at least 1 kg.

16. The method of claim 9, wherein the hardness is from 2 to 20 kg.

17. The method of claim 15, wherein the hardness is from 2 to 20 kg.

* * * * *